United States Patent [19]

Falk et al.

[11] Patent Number: 5,068,397

[45] Date of Patent: Nov. 26, 1991

[54] TRIS-PERFLUOROALKYL TERMINATED NEOPENTYL ALCOHOLS AND DERIVATIVES THEREFROM

[75] Inventors: Robert A. Falk, New City, N.Y.; Kirkland P. Clark, Bethel, Conn.; Michael Jacobson, Haworth, N.J.; Athanasios Karydas, New York; Juliana Rodgers, Staten Island, both of N.Y.

[73] Assignee: Ciba-Geigy Corporation, Ardsley, N.Y.

[21] Appl. No.: 567,852

[22] Filed: Aug. 15, 1990

[51] Int. Cl.$^5$ ............................................. C07C 309/04
[52] U.S. Cl. .................................... 560/150; 560/152; 560/170; 560/227; 564/96; 564/224; 564/503; 568/35; 568/39; 568/50; 568/55
[58] Field of Search ................. 568/35, 39, 50, 55; 564/96, 224, 503; 560/150, 152, 170, 227

[56] References Cited

U.S. PATENT DOCUMENTS

| | | | |
|---|---|---|---|
| 3,716,401 | 2/1973 | Axelrod | 520/385 |
| 3,856,849 | 12/1974 | Huber-Emden et al. | 560/220 |
| 3,923,715 | 12/1975 | Dettre et al. | 524/199 |
| 4,084,059 | 4/1978 | Katsushima et al. | 560/87 |
| 4,192,754 | 3/1980 | Marshall et al. | 252/8.8 |
| 4,264,484 | 4/1981 | Patel | 524/168 |
| 4,325,857 | 4/1982 | Champaneria et al. | 523/412 |
| 4,346,141 | 8/1982 | Remington | 428/289 |
| 4,388,372 | 6/1983 | Champaneria et al. | 428/395 |
| 4,517,376 | 5/1985 | Krahler et al. | 560/87 |
| 4,565,717 | 1/1986 | Hosegood et al. | 427/339 |
| 4,595,518 | 6/1986 | Raynolds et al. | 252/8.6 |
| 4,898,981 | 2/1990 | Falk | 568/28 |
| 4,946,992 | 8/1990 | Falk | 560/227 |

*Primary Examiner*—Joseph L. Schofer
*Assistant Examiner*—M. Nagumo
*Attorney, Agent, or Firm*—Kevin T. Mansfield; Edward McC. Roberts

[57] ABSTRACT

Tris-perfluoroalkyl terminated neopentyl alcohols of the formula $(R_f-E_n-X-CH_2)_3CCH_2OH$ prepared from halogenated neopentyl alcohols and thiols of the formula $R_f-E_n-SH$, amines of the formula $R_f-E_n-NH-R$, alcohols of the formula $R_f-E_n-OH$, perfluoro-acids or amides, are described. The alcohols react with isocyanates to prepare urethanes; with acids or derivatives, to prepare esters or carbonates; with epoxides to form ethers. Further, they may be converted to halide intermediates. The products all contain the residue of at least one $R_f$-neopentyl alcohol containing three perfluoroalkyl hetero groups.

12 Claims, No Drawings

TRIS-PERFLUOROALKYL TERMINATED NEOPENTYL ALCOHOLS AND DERIVATIVES THEREFROM

BACKGROUND OF THE INVENTION

This invention relates to hetero group containing perfluoroalkyl terminated neopentyl alcohols and their derived compositions, and their use to impart oil and water repellency to textiles, glass, paper, leather, and other substrates.

Tris-perfluoroalkyl terminated neopentyl alcohols have not been previously described. The subject perfluoroalkyl alcohols are readily isolated in high yield and purity and are thermally and hydrolytically stable. A major advantage of these tris-perfluroalkyl derivatives is that the perfluoro groups are spatially close and provide a particularly low free surface energy. Another advantage of the subject alcohols is that the pendant perfluoroalkyl chains are connected by flexible hetero groups to the remainder of the molecule thus providing more mobile perfluoroalkyl functions which can align better.

Certain tris-perfluoroalkyl type alcohols, containing ester functions have been described in U.S. Pat. Nos. 3,029,585, 4,084,059, 4,346,141, and 4,565,717.

Bis-perfluoroalkyl esters and amides of benzene polycarboxylic acids, particularly pyromellitates and tris-perfluoroalkyl citrates, have been used for yarn finishes. The fluorochemicals impart soil and stain resistance to carpeting made from polyolefin and nylon fibers. These fluorochemicals are described in U.S. Pat. Nos. 3,716,401, 3,856,849, 3,923,715, 4,019,585, 4,192,754, 4,264,484, 4,325,857, 4,388,372, 4,517,376, and 4,595,518.

These compounds are subject to hydrolysis and present a problem for long-term storage.

Tris-perfluoroalkyl alcohols and derivatives thereof are particularly useful because they possess a low free surface energy that provides oil and water repellency to a wide variety of substrates. Alcohols containing a single or dual $R_f$-function are known, but do not provide these repellency properties to the same extent. The subject alcohols may be prepared in high yield and purity. Most importantly the instant alcohols are stable.

DETAILED DISCLOSURE

This invention relates to a method of making tris-perfluoroalkyl terminated neopentyl alcohols. Another aspect of this invention relates to derived $R_f$-containing urethane, ether, ester, or carbonate-containing compositions or polymers having pendant tris-perfluoroalkyl terminated neopentyl moieties.

Another aspect of this invention relates to a substrate containing 0.01 to 10% by weight of a fluorine-containing composition, at least part of said fluorine being provided by one or more units derived from the heteroatom containing $R_f$-neopentyl alcohol.

The instant invention pertains to $R_f$-neopentyl alcohols and derivatives thereof having the formula:

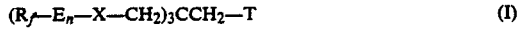     (I)

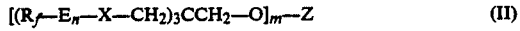     (II)

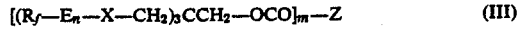     (III)

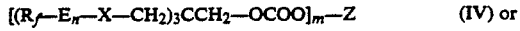     (IV) or $[(R_f-E_n-X-CH_2)_3CCH_2-OCONH]_m-Z$     (V)

where

T is —OH, —Cl, —Br, —I, or —SH, m is 1 to 6,

Z is an m-valent aliphatic, cycloaliphatic or aromatic radical, and Z in formula II is also —CO— when m is 2, and Z in formula III is also a direct bond when m is 2, wherein $R_f$ is independently a straight or branched chain perfluoroalkyl of 1 to 12 carbon atoms, perfluoroalkyl of 2 to 6 carbon atoms substituted by perfluoroalkoxy of 2 to 6 carbon atoms, or an oligo(hexafluoropropene oxide) terminal group, and n=1 or 0, and when n=1, E is independently a branched or straight chain alkylene of 1 to 10 carbon atoms or said alkylene interrupted by one to three groups selected from the group consisting of —NR—, —O—, —S—, $SO_2$—, —COO—, —OOC—, —CONR—, —NRCO—, —$SO_2$NR—, —NR$SO_2$—, or terminated at the $R_f$ end with —CONR— or —$SO_2$NR—, where R is attached to the carbon or sulfur atom, and X is —S—, —O—, —$SO_2$—, —NR—, or —$CO_2$—, and when n=0, X is a direct bond, —CONR— or —$SO_2$NR—, where $R_f$ is attached to the carbon or sulfur atom, and where R is independently hydrogen, alkyl of 1 to 6 carbon atoms or hydroxyalkyl of 2 to 6 carbon atoms.

Formula I denotes the instant alcohol as well as the corresponding halides, or mercaptans derived therefrom.

Formula II denotes ethers which are conveniently prepared from the instant alcohol of formula I and an epoxide or an alkyl halide compound.

Formula III denotes esters which are conveniently prepared by reaction of the instant alcohol of formula I with an acid halide or anhydride or by transesterification.

Formula IV denotes carbonates which are conveniently prepared by reaction of the instant alcohol of formula I with an appropriate chloroformate. When the alcohol of formula I is reacted with phosgene directly formula II can represent a carbonate as well where Z is —CO—.

Formula V represents urethanes which are conveniently prepared by reaction of the instant alcohol of formula I with an isocyanate.

The preferred compounds are those wherein $R_f$ is perfluoroalkyl of 6 to 12 carbon atoms, E is ethylene, and X is —S—.

Z is an m-valent radical which may be more specifically defined as follows:

when m is 1, Z is straight or branched chain alkyl of 1 to 36 carbon atoms, said alkyl substituted by hydroxyl or —$CH_2OH$ and interrupted by —O—, straight or branched chain alkenyl of 2 to 36 carbon atoms, cycloalkyl of 5 to 12 carbon atoms, aryl of 6 to 15 carbon atoms, said aryl or cycloalkyl substituted by phenyl or by alkyl of 1 to 9 carbon atoms, or Z is phenyalkyl of 7 to 15 carbon atoms;

when m is 2, Z is straight or branched chain alkylene of 1 to 18 carbon atoms, arylene of 6 to 15 carbon atoms, cycloalkyl of 5 to 12 carbon atoms, or said cycloalkyl or arylene substituted by alkyl of 1 to 9 carbon atoms, or Z is xylylene, or Z is alkylene-arylene-alkylene of 18 to 26 carbon atoms substituted in the alkylene by hydroxyl or —CH₂—OH and with the alkylene interrupted by —O—, when m is 3, Z is alkanetriyl of 3 to 8 carbon atoms or benzenetriyl or said benzenetriyl substituted by alkyl of 1 to 4 carbon atoms;

when m is 4, Z is alkanetetrayl of 4 to 9 carbon atoms, benzenetetrayl or benzenetetrayl substituted by alkyl of 1 to 4 carbon atoms;

when m is 5, Z is alkanepentayl of 5 to 9 carbon atoms; and when m is 6, Z is alkanehexayl of 6 to 12 carbon atoms, or cyclohexanehexayl.

Preferably when m is 1, Z is alkyl of 1 to 18 carbon atoms; alkenyl of 2 to 18 carbon atoms; cycloalkyl of 5 to 8 carbon atoms, aryl of 6 to 10 carbon atoms or phenylalkyl of 7 to 9 carbon atoms;

when m is 2, Z is alkylene of 2 to 12 carbon atoms; phenylene or

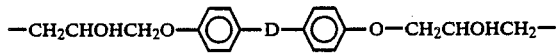

where D is a direct bond, —O—, —S—, —SO—, —SO₂, methylene or alkylidene of 2 to 8 carbon atoms; said alkylene substituted by hydroxyl or —CH₂OH and interrupted by —O—, when m is 3, Z is preferably glyceryl or trimethylyl propane;

when m is 4, Z is preferably pentaerythrityl or butane-1,2,3,4-tetrayl; and when m is 6, Z is preferably sorbityl, mannityl or inosityl.

Most preferably, when m is 1, Z is alkyl of 1 to 12 carbon atoms, alkenyl of 2 to 3 carbon atoms, cycloalkyl of 5 to 6 carbon atoms, phenyl or benzyl; and when m is 2, Z is most preferably alkylene of 2 to 12 carbon atoms, said alkylene substituted by hydroxyl or by —CH₂OH or a mixture thereof and interrupted by —O—; phenylene or

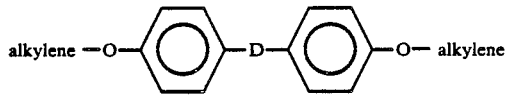

where D is isopropylidene and where the alkylene is substituted by hydroxyl or by —CH₂OH or a mixture thereof.

Preferably T is —OH or —Br; most preferably T is —OH.

The instant invention also pertains to a polymer which comprises the copolymerization product of (a) 0.1 to 100% by weight of a compound for formula VI

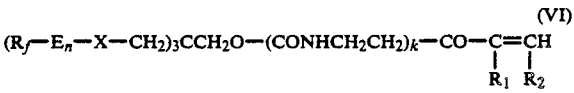

where k is 0 or 1, $R_1$ is hydrogen or methyl, $R_2$ is hydrogen, —COOH or —COOR₃ where $R_3$ is alkyl of 1 to 18 carbon atoms, wherein $R_f$ is independently a straight or branched chain perfluoroalkyl of 1 to 12 carbon atoms, perfluoroalkyl of 2 to 6 carbon atoms substituted by perfluoroalkoxy of 2 to 6 carbon atoms, or an oligo(hexafluoropropene oxide) terminal group, and n=1 or 0, and
when n=1, E is independently a branched or straight chain alkylene of 1 to 10 carbon atoms or said alkylene interrupted by one to three groups selected from the group consisting of —NR—, —O—, —S—, SO₂—, —COO—, —OOC—, —CONR—, —NRCO—, —SO₂NR—, —NRSO₂—, or terminated at the $R_f$ end with —CONR— or —SO₂NR—, where $R_f$ is attached to the carbon or sulfur atom, and X is —S—, —O—, —SO₂—, —NR—, or —CO₂—, and when n=0, X is a direct bond, —CONR— or —SO₂NR—, where $R_f$ is attached to the carbon or sulfur atom, and where R is independently hydrogen, alkyl of 1 to 6 carbon atoms or hydroxyalkyl of 2 to 6 carbon atoms, and, (b) 99.9 and 0% by weight of a vinyl monomer different from the compound of component (a).

Suitable hydrophilic monomers include, without limitation, hydroxy substituted lower alkyl acrylates and methacrylates, acrylamide, methacrylamide, $C_1$–$C_2$ or lower alkyl acrylamides and methacrylamides, ethoxylated acrylates and methacrylates, hydroxy substituted lower alkyl acrylamides and methacrylamides, hydroxy substituted lower alkyl vinyl ethers, sodium ethylene sulfonate, sodium styrene sulfonate, 2-acrylamido-2-methylpropanesulfonic acid, N-vinylpyrrole, N-vinyl succinimide, N-vinyl-2-pyrrolidone, 2- and 4-vinylpyridine, acrylic acid, methacrylic acid, amino including quaternary ammonium) substituted lower alkyl acrylates and methacrylates.

Preferably the hydrophilic vinyl monomers include 2-hydroxyethyl methacrylate, 2-hydroxyethyl acrylate, acrylamide, methacrylamide, N,N-dimethylacrylamide, N-vinyl-2-pyrrolidone, acrylic acid and methacrylic acid.

Suitable hydrophobic vinyl monomers include, without limitation, $C_1$–$C_{18}$ alkyl acrylates and methacrylates, acrylonitrile, styrene, vinyl alkanoates, vinyl alkyl ethers, alkenes and haloalkenes.

Preferably the hydrophobic vinyl monomers are methyl methacrylate and vinyl acetate.

It is understood that the $R_f$ group usually represents a mixture of perfluoroalkyl moieties. When the $R_f$ group is identified as having a certain number of carbon atoms, said $R_f$ group also usually concomitantly contains a small fraction of perfluoroalkyl groups with lower carbon atoms and a small fraction of perfluoroalkyl groups with higher carbon atoms. Commonly the perfluoroalkyl moiety is a mixture of $C_4F_9$—, $C_6F_{13}$—, $C_8F_{17}$—, $C_{10}F_{21}$—, $C_{12}F_{25}$—, and $C_{14}F_{29}$—.

The $R_f$ group also may be an oligo(hexafluoropropene oxide) based terminal group, where n=2–6 as described by Ishikawa, N. J. Fluorine Chem. 25 (27), 241–253 (1984), Ponomarenko, Kolloidn. Zh., 38 1130 (1976). or Bartlett in U.S. Pat. No. 3,621,059.

Preferably the instant compounds are those where $R_f$ is perfluoroalkyl of 6 to 12 carbon atoms or perfluoroalkyl of 2 to 6 carbon atoms substituted by perfluoroalkoxy of 2 to 6 carbon atoms, E is alkylene of 2 to 6 carbon atoms, —CONHCH₂CH₂—, CH₂CH₂N(CH₃)CH₂CH₂—, CH₂CH₂SO₂NHCH₂CH₂— or —SO₂NHCH₂CH₂—, X is —S— or SO₂, or —O—.

Most preferred are those compounds where $R_f$ is perfluoroalkyl of 6 to 12 carbon atoms, E is ethylene, and X is S, i.e., $(R_fCH_2CH_2SCH_2)_3CCH_2OH$ The novel $R_f$-alcohols can be obtained directly by the trihalogenated pentaerythritol of formula -

$(YCH_2)_3CCH_2OH$, where Y is Cl, Br, or I.

In one preferred embodiment, the neopentyl derivative is tribromopentaerythritol and has the formula $(BrCH_2)_3CCH_2OH$. This intermediate is commercially available in high purity. Trichloro, dichlorobromo-, and triiodo-neopentyl alcohols have also been reported.

The synthesis of $R_f$-alcohols proceeds by the nucleophilic substitution of a perfluoroalkyl substituted thiolate or amine for halide. The reaction may be conducted in an aqueous system using phase transfer catalysis, but work-up of such an aqueous product is difficult due to troublesome emulsions. The improved process of this invention involves the combination of:

a. an aprotic solvent, such as N-methylpyrrolidone, N,N-dimethylformamide, dimethyl sulfoxide, or the like, or ketones, such as acetone, methyl alkyl ketones, or dialkyl ketones. Chlorinated solvents and esters generally give poor conversions and are unsuitable;

b. moderate reaction temperatures, about 50° to about 120°C., and c. a stoichiometric quantity of an anhydrous alkaline earth carbonate, preferably potassium carbonate, in the ratio of 1 mole of carbonate per mole of halide to be displaced; and d. in the case of the amines, tertiary amine catalysis is useful as exemplified by triethylamine, tributylamine, dimethylaminopyridine, or piperidine.

e. in the case of the oxygenated ethers, carboxylates, or sulfonamides, Crown ether catalysis is useful as exemplified by 12-Crown-4, 15-Crown-5, and 18-Crown-6.

The reaction temperature, and choice of solvent are mutually dependent. A reaction temperature in the range of 50°-140° C. is one wherein the formation of undesirable by-products is minimized and wherein the reaction products are stable. Conditions are adjusted in order to achieve a reasonable rate of reaction at the chosen temperature.

It should be noted that the ready oxidation of thiols to disulfides requires that the chemistry be conducted in an inert atmosphere.

The subject alcohols can also be made by first reacting the bromoalcohol intermediates with a functional thiol, amine or alcohol, e.g. $HSCH_2CH=CH_2$, $HSCH_2COOH$ or $NH_2CH_2CH=CH_2$. The resultant intermediate can then be reacted with the $R_f$-containing moiety by a suitable chemistry that does not involve the pendant hydroxyl groups.

For example,

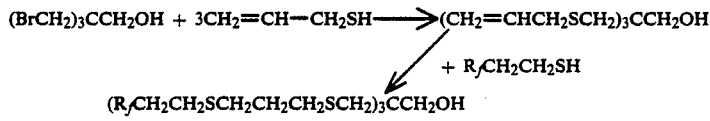

The $R_f$ moiety may be derived from $R_fI$, $R_fCH_2CH_2I$, $R_fCH_2CH_2OH$, or a like monofunctional $R_f$-reactant. If iodine atoms are introduced, they may be removed by reduction, dehydrohalogenation, or coupling.

In the case of sulfido-linked alcohols, they can be readily oxidized to the corresponding tris-sulfone alcohols by peracetic acid ($H_2O_2$/acetic acid) or by other conventional oxidants that selectively oxidize sulfides in the presence of alcohol functions. With peracetic acid, temperatures of 30°-100° C. are appropriate depending on the amount of excess oxidizing agent to ensure that the intermediate sulfoxides are completely oxidized.

The tris $R_f$-alcohols of this invention can be further reacted to form halides, which would be difficult to prepare otherwise. Such intermediates as $(R_f-E_n-X-CH_2)_3CCH_2Br$ have special utility and can be prepared with $PBr_3$. The chloro- derivatives can be synthesized in a conventional manner using $PCl_3$.

Perfluoroalkyl thiols useful herein are well documented in the prior art. For example, thiols of the formula $R_f-E-SH$ have been described inter alia U.S. Pat. Nos. 3,655,732 and 4,584,143.

Thus, U.S. Pat. No. 3,655,732 discloses mercaptans of formula: $R_f-E-SH$, where E is alkylene of 1 to 16 carbon atoms and $R_f$ is perfluoroalkyl, and teaches that halides of formula $R_f-E$-halide are well-known; reaction of $R_fI$ with ethylene under free-radical conditions gives $R_f(CH_2CH_2)_aI$ while reaction of $R_fCH_2I$ with ethylene gives $R_fCH_2(CH_2CH_2)_aI$ as is further taught in U.S. Pat. Nos. 3,088,849; 3,145,222; 2,965,659 and 2,972,638.

U.S. Pat. No. 3,655,732 further discloses compounds of formula $R_f-R'-Y-R''-SH$, where R' and R'' are alkylene of 1 to 16 carbon atoms, with the sum of the carbon atoms of R' and R'' being no greater than 25, $R_f$ is perfluoroalkyl of 4 through 14 carbon atoms and Y is —S— or —NR'''— where R''' is hydrogen or alkyl of 1 through 4 carbon atoms.

U.S. Pat. No. 3,544,663 teaches that the mercaptan $R_fCH_2CH_2SH$, where $R_f$ is perfluoroalkyl of 5 to 13 carbon atoms, can be prepared by reacting the perfluoroalkyl alkylene iodide with thiourea or by adding $H_2S$ to a perfluoroalkyl substituted ethylene ($R_f-CH=CH_2$), which in turn can be prepared by dehydrohalogenation of the halide $R_f-CH_2CH_2$-halide.

The reaction of the iodide $R_f-E-I$ with thiourea followed by hydrolysis to obtain the mercaptan $R_f-E-SH$ is the preferred synthetic route. The reaction is applicable to both linear and branched chain iodides.

Particularly preferred herein are the thiols of formula $R_fCH_2CH_2SH$, where $R_f$ is perfluoroalkyl of 6 to 12 carbon atoms. These $R_f$-thiols can be prepared from $R_fCH_2CH_2I$ and thiourea in very high yield.

Perfluoroalkylamines useful herein are well documented in the prior art. For example, $C_6F_{13}CH_2CH_2NH_2$ has been described in Japan Kokai 77/118,406. $R_fCH_2NH_2$, wherein $R_f$ is $CF_3$ through $CF_3(CF_2)_{11}$ are described in British Patent No. 717,232 (1954).

Further $R_fSO_2NR(CH_2)_nNR(CH_2)_3NH_2$ and $R_fCH_2CH_2SO_2NH(CH_2)_nNR_2$ are described in G.B.

1,106,641 and U.S. Pat. No. 3,838,165 respectively; R$_f$CONH(CH$_2$)$_n$NH$_2$ in Jap. Kokai 52/14767.

Perfluoroalkanols useful herein are well documented in the prior art and many are commercially available. They have the general formula R$_f$—E$_n$—OH and include:

C$_8$F$_{17}$SO$_2$N(C$_2$H$_5$)C$_2$H$_4$OH
C$_8$F$_{17}$C$_2$H$_4$OH
C$_7$F$_{15}$CH$_2$OH
C$_7$F$_{15}$CON(C$_2$H$_5$)C$_2$H$_4$OH
C$_8$F$_{17}$C$_2$H$_4$SC$_2$H$_4$OH
(CF$_3$)$_2$CF(CF$_2$)$_8$C$_2$H$_4$OH
(CF$_3$)$_2$CFOC$_2$F$_4$C$_2$H$_4$OH
C$_8$F$_{17}$C$_2$H$_4$SO$_2$N(CH$_3$)C$_4$H$_8$OH
C$_8$F$_{17}$CH$_2$OH
CF$_3$CH$_2$OH
C$_8$F$_{17}$CH$_2$CH$_2$SO$_2$NHCH$_2$CH$_2$OH

Perfluoroalkylsulfonamides useful herein are well documented in the prior art such as in U.S. Pat. No. 2,915,554 and include compounds of the general structure R$_f$—SO$_2$NHR, such as:

C$_8$F$_{17}$SO$_2$N(C$_2$H$_5$)H
C$_8$F$_{17}$SO$_2$N(CH$_3$)H
C$_8$F$_{17}$SO$_2$N(i—C$_3$H$_7$)H
C$_{10}$F$_{21}$SO$_2$N(C$_2$H$_5$)H
C$_{10}$F$_{21}$SO$_2$NH$_2$

Perfluoroacids useful herein include R$_f$—E$_n$—CO$_2$H, wherein E$_n$ is as previously described.

As used herein the term "urethane composition" means compounds and compositions that contain the characteristic

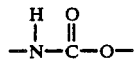

linkage and at least one tris —R$_f$— group.

Preferred urethane compositions include those where R$_f$ and E have the configurations previously described as being preferred and X is S, SO$_2$, or O.

These compositions have extremely low free surface energies and therefore, possess oil and water repellent properties, and mold release and other properties associated with low free surface energy. It should be noted that the compositions of this invention are characterized by the presence of three perfluoroalkylhetero groups near each other, a characteristic that provides improved oil and water repellent properties over the mono- or bis-fluorinated compositions of the prior art. Further the three perfluoroalkylthio groups are connected via a neopentyl moiety that does not permit the thermal elimination of mercaptan by betaelimination. Hence, these R$_f$-alcohols and derivatives have enhanced thermal stability.

Any convenient isocyanate can be used to react with the R$_f$-alcohol or R$_f$-containing hydroxy-terminated prepolymer. Myriads of useful isocyanates are well-known in the art.

Thus, one can use aliphatic or aromatic isocyanates, diisocyanates, triisocyanates and polyisocyanates.

Useful aromatic diisocyanates can be represented by the formula:

A(NCO)$_2$, where

A is phenylene that is unsubstituted or substituted by one or two alkyls of 1 to 4 carbon atoms, alkoxy of 1 to 4 carbon atoms, chloro, bromo and nitro, naphthylene that is unsubstituted or substituted by one or two of alkyl of 1 to 4 carbon atoms, chloro, bromo and nitro, or where A is a group of formula:

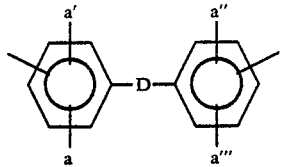

where

D is a direct bond, oxygen, methylene or ethylene, and a, a', a'' and a''' each independently are hydrogen, alkyl of 1 to 4 carbon atoms, alkoxy of 1 to 4 carbon atoms, chloro or bromo.

Aromatic triisocyanates can be represented by the formula

G(NCO)$_3$ where G is benzenetriyl or substituted benzenetriyl group.

Aromatic di- and triisocyanates as described above include tolylene diisocyanate (TDI) (all isomers), 4,4'-diphenylmethane diisocyanate (MDI), tolidine diisocyanate, dianisidine diisocyanate, m-xylylene diisocyanate, p-phenylene diisocyanate, m-phenylene diisocyanate, 1-chloro-2,4-phenylene diisocyanate, 3,3'-dimethyl-4,4'-bisphenylene diisocyanate, 4,4'-bis(2-methylisocyanatophenyl)methane, 4,4'-bisphenylene diisocyanate, 4,4'-bis-(2-methoxyisocyanatophenyl)methane, 1-nitro-phenyl-3,5-diisocyanate, 4,4'-diisocyanatodiphenyl ether, 3,3'-dichloro-4,4'-diisocyanatodiphenyl ether, 3,3'-dichloro,4,4'-diisocyanatodiphenyl-methane, 4,4'-diisocyanatodibenzyl, 3,3'-dimethoxy-4,4'-diisocyanatodiphenyl, 2,2'-dimethyl-4,4'-diisocyanatodiphenyl, 2,2'-dichloro-5,5'-dimethoxy-4,4'-diisocyanatodiphenyl, 3,3'-dichloro-4,4'-diisocyanatodiphenyl benzene-1,2,4-triisocyanate, benzene-1,3,5-triisocyanate, benzene-1,2,3-triisocyanate, toluene 2,4,6-triisocyanate, toluene 2,3,4-triisocyanate, 1,2-naphthalene diisocyanate, 4-chloro-1,2-naphthalene diisocyanate, 4-methyl-1,2-naphthalene diisocyanate, 1,5-naphthalene diisocyanate, 1,6-naphthalene diisocyanate, 1,7-naphthalene diisocyanate, 1,8-naphthalene diisocyanate, 4-chloro-1,8-naphthalene diisocyanate, 2,3-naphthalene diisocyanate, 2,7-naphthalene diisocyanate, 1,8-dinitro-2,7-naphthalene diisocyanate, 1-methyl-2,4-naphthalene diisocyanate, 1-methyl-5,7-naphthalene diisocyanate, 6-methyl-1,3-naphthalene diisocyanate, 7-methyl-1,3-naphthalene diisocyanate, polymethylene polyphenyl isocyanate and co-products of hexamethylene diisocyanate and tolylene diisocyanate.

Useful aliphatic diisocyanates include those of general formula

L(NCO)$_2$ where

L is straight or branched chain alkylene of 2 to 16 carbon atoms, optionally containing halides or cycloaliphatic functions.

Useful aliphatic or cycloaliphatic polyisocyanates include—1,2-ethane diisocyanate, 1,3-propane diisocyanate, 1,4-butane diisocyanate, 2-chloropropane-1,3-diisocyanate, pentamethylene diisocyanate, propylene-1,2-diisocyanate, 1,6-hexane diisocyanate. 1,8-octane diisocyanate, 1,10-decane diisocyanate, 1,12-dodecane diisocyanate, 1,16-hexadecane diisocyanate and other aliphatic diisocyanates such as 1,3-cyclohexane diisocyanate, 1,4-cyclohexane diisocyanate, cyclohexane triisocyanate, 4,4'-methylene bis(cyclohexyl isocyanate), isophorone diisocyanate.

Additionally, the following diisocyanates are particularly preferred because urethane compositions made therefrom tend to be non-yellowing:

1,6-hexamethylene diisocyanate (HDI), 2,2,4- and 2,4,4-trimethylhexaethylene diisocyanate (TMDI), dimer acid derived diisocyanate (DDI) obtained from dimerized fatty acids, such as linoleic acid 4,4'-dicyclohexylmethane diisocyanate (hydrogenated MDI), isophorone diisocyanate, 3-isocyanatomethyl-3,5,5-trimethylcyclohexyl diisocyanate, lysine methyl ester diisocyanate (LDIM), bis(2-isocyanatoethyl) fumarate (FDI), bis(2-isocyanatoethyl) carbonate, m-tetramethylxylylene diisocyanate (TMXDI), Polyisocyanates include polymethylene polyphenylisocyanate (PAPI) and tris-(isocyanatophenyl) thiophosphate (Desmodur).

Besides the reaction with polyisocyanates, useful urethane compositions can be obtained from the aliphatic and aromatic monoisocyanates.

Some useful aromatic monoisocyanates include -2-fluorophenyl isocyanate, 3-fluorophenyl isocyanate, 4-fluorophenyl isocyanate, m-fluorosulfonylphenyl isocyanate, trans-2-phenylcyclopropyl isocyanate, m-tolyl isocyanate, p-tolyl isocyanate, 1,1,1-trifluoro-o-tolyl isocyanate, 1,1-trifluoro-m-tolyl isocyanate, p-bromophenyl isocyanate, 2,5-dimethylphenyl isocyanate, o-ethoxyphenyl isocyanate, p-ethoxyphenyl isocyanate, o-methoxyphenyl isocyanate, m-methoxyphenyl isocyanate, p-methoxyphenyl isocyanate, 1-naphthyl isocyanate, o-nitrophenyl isocyanate, m-nitrophenyl isocyanate, p-nitrophenyl isocyanate, p-phenyl azophenyl isocyanate, o-tolyl isocyanate.

Useful aliphatic or cycloaliphatic monoisocyanates include such alkyl isocyanates of 1 to 16 carbon atoms as methyl isocyanate, ethyl isocyanate, n-propyl isocyanate, n-butyl isocyanate, t-butyl isocyanate, hexyl isocyanate, octyl isocyanate, 2-dodecyl isocyanate, octadecyl isocyanate, hexadecyl isocyanate and mixtures thereof, as well as cyclohexyl isocyanate, m-isopropenyldimethyl benzyl isocyanate (TMI), and 2-isocyanatoethyl methacrylate (IEM).

Besides addition to the formation of the urethane compositions described above, the R$_f$-alcohols described herein can be converted to the corresponding chloroformate by treatment with chlorocarbonyl pyridinium chloride or phosgene:

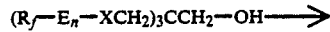

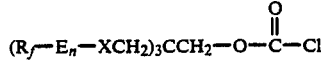

which in turn can be reacted with an appropriate amine to yield a urethane.

The reaction between the isocyanate component and the hydroxyl component can be carried out in bulk, i.e., without solvent, or in the presence of non-reactive, anhydrous organic solvents. Solvent media in which the reaction can be carried out include ketones, such as acetone, methyl ethyl ketone and methyl isobutyl ketone; esters such as ethyl acetate, isopropyl acetate, butyl acetate, 2-ethylhexyl acetate; hydrocarbons such as hexane, heptane, octane and higher homologs, cyclohexane, benzene, toluene, xylene or blends of aliphatic, cycloaliphatic and aromatic hydrocarbons or aprotic solvents such as N-methylpyrrolidone; it is also possible to employ ethers, both aliphatic and alicyclic including di-n-propyl ether, di-butyl ether, tetrahydrofuran and the diethers of polyalkylene oxides. In addition, chlorinated solvents such as 1,1,1-trichloroethane, dichloroethyl ether, ethylene dichloride, perchloroethylene and carbon tetrachloride can be used.

In all cases, the solvents should be anhydrous to avoid urea formation.

The reaction can, if desired, be catalyzed and those catalysts conventionally employed in the urethane art are useful herein. Useful catalysts fall principally in two groupsa. Amino compounds and other bases:
triethylamine and other trialkylamines, triethylenediamine, 1,4-diaza-2,2,2-bicyclooctane, N-(lower)alkylmorpholines, N,N,N',N'-tetramethyl-ethylenediamine, N,N,N',N'-tetramethyl-1,3-butanediamine, substituted piperazines, dialkylalkanolamines, benzyltrimethylammonium chloride and b. Organometallic and inorganic compounds:
cobalt naphthenate, stannous chloride, stannous octoate, stannous oleate, dimethyl tin dichloride, di-n-butyltin dilaurylmercaptide, tetra-n-butyl-tin, trimethyl-tin hydroxide, di-n-butyltin dilaurate.

Such catalysts may be used singly or in combination with each other. Beneficial synergistic catalysis may occur when combinations are used.

It is possible to carry out the reaction without the use of a catalyst; it is preferable for reasons of economy and completeness to utilize one or more catalysts as listed, in amounts ranging from 0.001 to 1% based on the weight of the reactants. It is similarly advantageous to carry out the urethane synthesis at elevated temperature, usually between room temperature and 120° C. and preferably at 60° C. to 80° C. to obtain a complete reaction between 0.5 to 8 hours reaction time.

The reaction can be easily followed by titration of the isocyanate group or by IR analysis.

The usefulness of the urethane compositions is determined by measuring the oil, water and soil repellency ratings of substrates such as fabrics, paper, carpeting, leather, etc. that are treated with solutions or emulsions of the novel urethane compositions.

These urethane compositions can be applied, from a dilute solution in suitable a solvent such as the fluoroalkanes, fluorochloroalkanes, chlorinated alkanes or aromatics, hydrocarbon aromatics, ketones, ester and others. Concentrations of the fluorinated compound in the solvent can be adjusted to provide an amount of urethane composition deposited on the substrate sufficient to provide oil and water repellency. This amounts to a deposit of from 0.01 to 10%, preferably from 0.1 to 1%, of urethane composition, based on the weight of substrate.

The urethane solution may be applied by any of the known techniques such as by dipping, spraying, brushing, padding, roll coating or by any desired combination of such techniques. The optimum method of application will depend principally on the type of substrate being coated.

Coatings of the urethane compositions of the invention may be applied to any desired substrate, porous or non-porous. They are particularly suited for application to porous materials such as textiles, carpeting, leather, paper, wood, masonry, unglazed porcelain and the like to provide valuable oil and water repellency properties. However, they may also be applied to non-porous materials such as metals, plastics, glass, painted surfaces and the like to provide similar oil and water repellency properties. More specifically the urethane compositions of the invention act as leveling, wetting and spreading agents in formulations designed for application to floors, furniture and automobiles. In such applications a protective oil and water repellent film is left on the treated object after the removal of the bulk of the material. Such leveling, wetting, spreading and film forming properties are also useful in:

a. formulations for cleaning glass and other hard, non-porous materials b. hair care products such as rinses, shampoos, and sprays.

c. paint, stain and varnish formulations for application to wood, masonry and ceramics.

In the treatment of paper, the urethane compositions may be present as an ingredient in a wax, starch, casein, elastomer, or wet strength resin formulation. Aqueous emulsions of the urethane compositions are especially useful in the treatment of paper. By mixing the urethane compositions in an aqueous or oil type paint formulation, it may be applied effectively to unpainted asbestos siding, wood, metal and masonry. In the treatment of floors and tile surfaces and like substrates, and urethane compositions may be applied by their incorporation in an emulsion or solution.

Because of the ability of the surfaces treated with these urethane compositions to withstand abrasive action, the repellency to oil and water and their resistance to soiling is markedly improved. Preferred classes of articles to be treated are papers and textiles. Illustrative papers are carbonizing ti$sue, wallpaper, asphalt laminates, liner board, cardboard and papers derived from synthetic fibers.

Any types of textile materials, such as cotton, wool, fiber glass, silk, regenerated cellulose, cellulose esters, cellulose ethers, polyesters, polyamides, polyolefins, polyacrylonitrile, polyacrylic esters, inorganic fibers, etc. either alone or blended in any combination may be successfully coated with the urethane compositions of the invention. The resulting textile material will be found to be repellent to water and oil, and the textile material will retain its resistance to such agents even after many launderings and dry cleanings.

It will be often advantageous to use the urethane compositions of the invention in combination with conventional finishes, such as mildew preventatives, moth resisting agents, crease resistant resins, lubricants, softeners, fat liquors, sizes, flame retardants, antistatic agents, dye fixatives and water repellents.

TEST METHODS

The critical surface tensions are determined by contact angle measurements as described by W. Zisman, *Contact Angles*, Advances in Chemistry, No. 43, ACS Publications, Washington, D.C., 1964.

The AATCC water spray test rating was determined according to Standard Test method 22-1985 of the American Association of Textile Chemists and Colorists, Volume 61, 1986 (also designated ASTM-D-583-58). Ratings are given from 0 (minimum, worst) to 100 (maximum, best).

The AATCC Oil Rating was determined according to Standard Test method 118-1983 of the American Association of Textile Chemists and Colorists. Ratings are given from 0 (minimum, worst) to 8 (maximum) best. A commonly accepted level of repellency for oil repellent fabrics in the United States is an oil repellency of 4.

The dry soil test rating was determined according to the CIBA-GEIGY Internal Test for Accelerated Dry Soiling. Ratings are given from 0 (minimum, worst) to 100 (maximum, best) according to this test 10 treated and 2 untreated fabric samples ($2\frac{1}{2}''\times 3\frac{1}{2}''$) are shaken in a $16''\times 24''$ plastic bag with 7 g of standard dry soil for a specific time. Excess soil is then removed from the fabrics under controlled conditions and the soiled fabrics are then visually compared to standards. The soil has the following composition:

| | |
|---|---|
| 38% | Peat Moss (Michigan Peat Inc., Capac Mich.) |
| 17% | Cement (Portland Cement) |
| 17% | Coolin Clay, Peerless (R. T. Vanderbilt Co., NY) |
| 17% | Silica (Floated Powder ~240 Mesh, Fisher Scientific) |
| 17.5% | Molaco Furnace (Binney & Smith Co., NY, NY) |
| 0.50% | Red Iron Oxide (C. K. Williams Co., Easton, PA) |
| 8.75% | Mineral Oil (Squibb) or Nujol (Plough, Inc.) |

The AATCC abrasion test rating was determined according to Standard Crockmeter Test method 8-1985 of the American Association of Textile Chemists and Colorists. Ratings are given from 0 (minimum, worst) to 8 (maximum, best).

All mentioned AATCC Tests are listed in the Technical manual of the American Association of Textile Chemists and Colorists, Volume 61, edition 1986.

EMULSIFICATION PROCEDURE

The urethanes of Examples 22-36 are emulsified using the following procedure. A 70° C. solution of 20.0 g urethane solids and 28.0 g isopropyl acetate is added to a 70° C. solution of 1.6 g N,N-dimethyl-1-octadecylammonium acetate in 77.3 g distilled water under high shear using a Polytron mixer. The mixture is sheared for 2 minutes and then homogenized for 5 minutes using a Microfluidizer unit Model NIIO (5500 psi, bath 5=40° C.). The isopropyl acetate and some water are removed from the pre-emulsion under vacuum (25 in Hg) at 50° C. using a roto-evaporator to yield a 10-20% solids emulsion.

APPLICATION METHOD

The emulsions are prediluted to 30% solids with distilled water. The ALKANOL ® wetting agent a high molecular weight alcohol supplied by DuPont, (0.2% on weight of bath) and more distilled water are added to apply 0.1% fluorine on weight of fabric at 48% wet pick-up. These baths are pad applied to SUPPLEX ® Nylon (DuPont) using a 1 dip, 1 nip application. The padded nylon is air dried and then oven cured at 171° C. for 2 minutes. Performance results are summarized in Table 1.

The invention described above is illustrated by the following examples:

Examples 1 to 6 illustrate the preparation of the $R_f$-alcohols.

Example 7 describes the use of the subject alcohols to prepare halides.

Example 8 demonstrates the preparation of a monomer from the subject alcohols.

Example 9 illustrates the utility of compositions derived from tris-$R_f$ alcohols.

Examples 10 to 20 describe other alcohols and derived products which are prepared similarly.

Examples 21 to 37 describe performance results of alcohols and derived urethanes.

Examples 38 and 39 describe derived epoxide adducts.

EXAMPLE 1

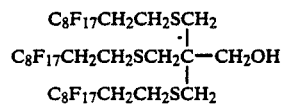

3-(1,1,2,2-Tetrahydroperfluorodecylthio)-2,2-bis-(1,1,2,2-tetrahydroperfluorodecylthiomethyl)-1-propanol 3-Bromo-2,2-bis(bromomethyl)-1-propanol (17.9 g, 0.055 mol) is charged to a five-necked flask with 1,1,2,2-tetrahydroperfluorodecylmercaptan (76.8 g, 0.16 mol) and potassium carbonate (22.1 g, 0.16 mol). Methyl propyl ketone (28.5 g) is added, and stirring is begun under nitrogen gas flow. The mixture is heated at 120° C. for 22 hours. GLC shows incomplete reaction. An additional 18.0 g mercaptan and 10.0 g potassium carbonate are added, and the mixture is heated and stirred at 120° C. for an additional 6 hours. Distilled water (100 g) is added to the reaction flask, and the warmed mixture is poured into a separatory funnel. The bottom layer, containing the product, is separated off and dried over anhydrous magnesium sulfate. This solution is gravity filtered and chilled, and the product is collected and crystallized twice from toluene. GLC showed 95% product, which is a white solid with m.p. 72°–74° C. Analysis for $C_{35}H_{21}F_{51}O_3S$:

Calculated: C, 27.6; H, 1.4; S, 6.3; F, 63.6.
Found: C, 27.3; H, 1.3; S, 6.8; F, 62.9.

EXAMPLE 2

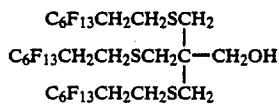

3-(1,1,2,2-Tetrahydroperfluorooctylthio)-2,2-bis-(1,1,2,2-tetrahydroperfluorooctylthiomethyl)-1-propanol 3-Bromo-2,2-bis(bromomethyl)-1-propanol (12.2 g, 0.038 mol) is charged in a five-necked flask with 1,1,2,2-tetrahydroperfluorooctylmercaptan (48.3 g, 0.13 mol) and potassium carbonate (16.7 g, 0.12 mol). Methyl propyl ketone (22.4 g) is added, and stirring is begun under nitrogen gas flow. The mixture is heated at 120° C. for 22 hours. Distilled water (50 g) is added to the reaction flask, and the mixture is warmed to 70° C. and then poured into a separatory funnel. The bottom layer, containing the product, is separated off and washed a second time with water After gravity filtration, the solvent is removed under vacuum. The crude product is a brown liquid (50.8 g) of 65% purity. Low boiling impurities are removed under high vacuum in a Kugelruhr apparatus to 120° C. The final product is a brown oil of 94% purity by GLC.

EXAMPLE 3

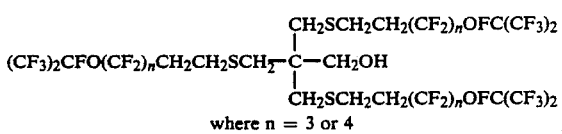

where n = 3 or 4

3-(ω-Heptafluoriosopropoxy-1,1,2,2-tetrahydroperfluoroalkylthio)-2,2-bis(ω-heptafluoroisopropoxy-1,1,2,2-tetrahydroperfluoroalkylthiomethyl)-1-propanol ω-Heptafluoroisopropoxy-1,1,2,2-tetrahydroperfluoro-alkanethiol (consisting of 73% n=3 homolog and 29% n=4 homolog) (12.0 g, 0.022 mol), 3-bromo-2,2-bis(bromomethyl)-1-propanol (2.27 g, 0.0069 mol), potassium carbonate (5.0 g, 0.036 mol) and methyl propyl ketone 10.0 g) are charged to a three-necked flask. The mixture is heated to 120° C. for 21 hours with agitation under nitrogen. Periodically, methyl propyl ketone (approx. 5 g) is added to replenish solvent loss. The crude product shows 67% purity by GLC. For analytical purposes, the product is stirred at 90° C. and washed with a 20 ml portion of distilled water. The layers are separated, and the solvent is evaporated from the organic layer, yielding a yellow oil (10.92 g). The sample is analyzed by GC/MS using a 15 m. capillary column programmed from 60°–250° C. at 8°/min. Two major components are observed.

(Triadduct alcohol with n=3).
  MS (C.I.)=1720
  MS (E.I.)=m/z 559 ($C_{12}H_6F_{19}O_1S_1$), 1207 ($C_{27}H_{17}F_{38}O_3S_2$).
(Triadduct alcohol with n=3 and 4 in ratio of 2:1, respectively)
  MS (C.I.)=1820
  MS (E.I.)=m/z 559 ($C_{12}H_6F_{19}O_1S_1$), 659 ($C_{14}H_6F_{23}O_1S_1$), 1307 ($C_{29}H_{17}F_{42}O_3S_3$)

In addition, an ion at m/z 741 along with small ions at m/z 1254 and 1256, suggests the presence of some diadduct mono-bromo alcohol with n=3. The mono bromo higher homolog also appears present with n=3 and 4.

EXAMPLE 4

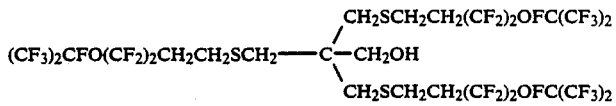

3-(4-Heptafluoroisopropoxy-1,1,2,2-tetrahydroperfluorobutanethio)-2,2-bis-(4-heptafluoroisopropoxy-1,1,2,2-tetrahydroperfluorobutanethiomethyl)-1-propanol 4-Heptafluoroisopropoxy-1,1,2,2-tetrahydroperfluoro-butanethiol (11.0 g, 0.032 mol), 3-bromo-2,2-bis(-bromomethyl)-1-propanol (3.2 g, 0.010 mol), potassium carbonate (4.0 g, 0.029 mol) and methyl propyl ketone (6.0 g) are charged to a three-necked flask. The mixture is heated to 120° C. for 25 hours with agitation under nitrogen periodically, methyl propyl ketone (approx. 5 g) is added to replenish solvent loss. The crude product shows 70% purity by GLC. For analytical purposes, the product is stirred at 70° C. and washed with a 20 ml. portion of distilled water. The layers are separated, and the solvent is evaporated from the organic layer, yielding a yellow oil (8.1 g, 72.3% of theory). The sample was analyzed by GC/MS using a 15 m. DB-1 capillary column programmed from 60°-250° C. at 8°/min. Three components are identified, with the major one being the trisubstituted alcohol:

(Oxetane Structure)
MS (C.I.)=774 (M+H)+
MS (E.I.)=m/z 359 ($C_8H_6F_{11}O_1S_1$), 424 ($C_{12}H_{12}F_{11}O_2S_1$), 461 ($C_{12}H_{12}F_{11}O_2S_2$)
(Diadduct mono bromo alcohol)
MS (C.I.)=854 (M+H)+
MS (E.I.)=m/z 359 ($C_8H_6F_{11}O_1S_1$), 509 ($C_{12}H_{13}Br_1F_{11}O_2S_1$), 541 ($C_{12}H_{13}Br_1F_{11}O_2S_2$)
(Triadduct alcohol)
MS (C.I.)=1120 (M+H)+
MS (E.I.)=m/z 359 ($C_8H_6F_{11}O_1S_1$), 807 ($C_{19}H_{17}F_{22}O_3S_2$)

The alcohol of Example 2 is prepared with other $R_f$ distributions, using the same procedure.

| | $R_f$ Distribution of Alcohol | | | | |
|---|---|---|---|---|---|
| Example | $C_6F_{13}$ | $C_8F_{17}$ | $C_{10}F_{21}$ | $C_{12}F_{25}$ | $C_{14}F_{29}$ |
| 5 | 35% | 34% | 20% | 9% | 2% |
| 6 | 2% | 48% | 32% | 14% | 4% |

EXAMPLE 7

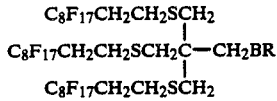

3-(1,1,2,2-Tetrahydroperfluorodecylthio)-2,2-bis-(1,1,2,2-tetrahydroperfluorodecylthiomethyl)-1-bromopropane 3-(1,1,2,2-Tetrahydroperfluorodecylthio)-2,2-bis-(1,1,2,2-tetrahydro-perfluorodecylthiomethyl)-1-propanol (10.0 g., 6.6 mmol) is charged to a three necked flask with phosphorous tribromide (4.3 g., 16 mmol). The reaction mixture is heated at 100° C. under nitrogen for 2 hours to give the desired product, which is recrystallized from toluene. Identification is made by GC/MS (EI mode).

EXAMPLE 8

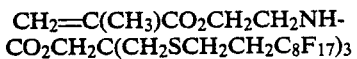

2-[3-(1,1,2,2-Tetrahydroperfluorodecylthio)-2,2-bis(1,1,2,2-tetrahydroperfluorodecylthiomethyl)-1-propyloxycarbonylamino]ethyl methacrylate 3-(1,1,2,2-Tetrahydroperfluorodecylthio)-2,2-bis(1,1,2,2-tetrahydroperfluorodecylthiomethyl)-1-propanol (10.0 g, 6.57 mmol) is charged in a three-necked flask with a catalytic amount of neopentanetetrayl tetrakis-(3,5-di-tert-butyl-4-hydroxyhydrocinnamate). A condenser fitted with a drying tube is placed in one neck and hexane (200.0 ml, dried), 2-isocyanato-ethyl methacrylate (1.13 g, 7.30 mmol), dibutyltin dilaurate (1.0 ml) and triethylamine (0.5 ml) are charged successively to the flask. With the bath temperature at 50°-55° C. and nitrogen gas flowing, the reaction mixture is heated for 18 hours. The procedure yields a white solid (10.2 g, 92% of theory) with a melting point of 80°-82° C.

Analysis for $C_{42}H_{30}F_5NO_4S_3$:
Calc: C, 30.1; H, 1.9; N, 0.83; S, 5.7; F, 57.7
Found: C, 30.2; H, 1.7; N, 1.1; S, 5.9; F, 56.4.

EXAMPLE 9

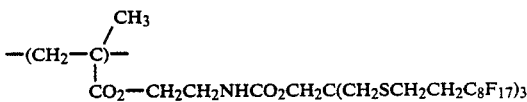

Poly(2-[3-(1,1,2,2-Tetrahydroperfluorodecylthio)-2,2-Bis-(1,1,2,2-tetrahydroperfluorodecylthiomethyl)-1-Propyloxycarbonylamino]ethyl methacrylate)

The monomer of Example 8 is polymerized with a photoinitiator and U.V. light in hexafluoroxylene. The polymer has a $\gamma_c$ of 11.0 dynes/cm quite comparable to the best of prior-art $R_f$-(meth)acrylate polymers as reported by pittman, A., J. Polymer Sci., 6, 1729-40 (1968).

Using the methods described and by techniques similar to Examples 1-8, the following additional alcohols and derivatives thereof are prepared.

EXAMPLES 10 to 20

| Ex. | Tris-$R_f$-Terminated Neopentyl Alcohols and Derivatives |
|---|---|
| 10 | $(CF_3CF_2CH_2OCH_2)_3CCH_2OH$ |
| 11 | $(C_6F_{13}(CH_2)_4SO_2CH_2)_3CCH_2OH$ |
| 12 | $(C_8F_{17}CH_2CH_2CH_2SCH_2)_3CCH_2Br$ |
| 13 | $(C_8F_{17}SO_2N(C_2H_5)CH_2)_3CCH_2OH$ |
| 14 | $(C_8F_{17}SO_2NHCH_2CH_2OCH_2)_3CCH_2OH$ |
| 15 | $(C_8F_{17}CH_2CH_2SO_2NHCH_2CH_2OCH_2)_3CCH_2OH$ |
| 16 | $(C_8F_{17}CH_2CH_2OCH_2)_3CCH_2OH$ |
| 17 | $(C_7F_{15}CONHCH_2CH_2SCH_2)_3CCH_2OH$ |
| 18 | $CH_2=C(CH_3)CO_2CH_2CH_2NHCO_2CH_2C(CH_2OCH_2CH_2C_8F_{17})_3$ |
| 19 | $CH_2=C(CH_3)CO_2CH_2C(CH_2SCH_2CH_2C_8F_{17})_3$ |
| 20 | $CH_2=CHCO_2CH_2C(CH_2OCH_2CH_2C_6F_{13})_3$ |

EXAMPLE 21

Performance Results on SUPPLEX Nylon 0.1% Fluorine on Weight of Fabric

| Example | AATCC Spray[1] | Oil Kit[2] | Dry Soil[3] | Abrasion Test[4] 10X | 20X | 30X |
|---|---|---|---|---|---|---|
| 5 | 50− | 0 | 75 | 0 | 0 | 0 |
| 6 | 50+ | 0 | 75 | 0 | 0 | 0 |
| Untreated | 0 | 0 | 0 | 0 | 0 | 0 |

[1]Spray Rating Method AATCC 22-1980
[2]Oil Kit Rating Method AATCC 118-1983
[3]Accelerated Dry Soiling Method - CIGA-GEIGY Internal Test
[4]Crockmeter Method AATCC 8-1985

In the above examples, the dry soil rating of greater than 50 demonstrates a substantial resistance to soil staining.

The finishes render the untreated fabric water repellent ($A^2$ spray > 8).

EXAMPLE 22

To a 1 liter jacketed reactor equipped with mechanical stirrer, water condenser, nitrogen inlet/outlet, and thermocouple is added 99.0 g (0.066 mols) $(C_8F_{17}CH_2CH_2SCH_2)_3CCH_2OH$ and 183 g isopropyl acetate. The solution is heated at reflux (85°–90° C.) and 35.4 g solvent is removed. The solution is cooled to 80° C. Then 5.65 g (0.033 mols) hexamethylene diisocyanate, 1.30 g isopropyl acetate and a solution of 0.20 g (0.0005 mols) stannous octoate in 1.80 g isopropyl acetate are added to the reactor and the reaction mixture is heated at 80° C. for 1.5 hours. All isocyanate is consumed as determined by I.R. Solvent removal yields the following product in quantitative yield.

$(C_8F_{17}CH_2CH_2SCH_2)_3CCH_2OCONH(CH_2)_6NH-COO-CH_2C(CH_2SCH_2CH_2C_8F_{17})_3$

The following urethanes were prepared according to the procedure described in Example 22.

| | | Rf Distribution of Alcohol | | | | |
|---|---|---|---|---|---|---|
| Example | $C_6F_{13}$ | $C_8F_{17}$ | $C_{10}F_{21}$ | $C_{12}F_{29}$ | $C_{14}F_{29}$ | Tri-or-Diisocyanate |
| 23 | — | 100% | — | — | — | Dimer Acid Diisocyanate |
| 24 | — | 100% | — | — | — | Trimethylhexamethylene diisocyanate |
| 25 | — | 100% | — | — | — | Isophorone diisocyanate |
| 26 | — | 100% | — | — | — | α, α, α', α'-tetramethyl m-xylylene diisocyanate |
| 27 | — | 100% | — | — | — | Dicyclohexylmethane-4,4'-diisocyanate (HMDI) |
| 28 | — | 100% | — | — | — | Diphenylmethane-4,4'-diisocyanate |
| 29 | — | 100% | — | — | — | Hexamethylene diisocyanate |
| 30 | — | 100% | — | — | — | Isophorone diisocyanate trimer |
| 31 | — | 100% | — | — | — | Hexamethylene diisocyanate trimer |
| 32 | 35% | 34% | 20% | 9% | 2% | Hexamethylene diisocyanate |
| 33 | 35% | 34% | 20% | 9% | 2% | Dimer Acid Diisocyanate |
| 34 | 35% | 48% | 32% | 14% | 4% | Dimer Acid Diisocyanate |
| 35 | 2% | 48% | 32% | 14% | 4% | Hexamethylene diisocyanate trimer |
| 36 | 2% | 48% | 32% | 14% | 4% | Isophorone diisocyanate trimer |

EXAMPLE 37

Performance Results on SUPPLEX Nylon 0.1% Fluorine on Weight of Fabric

| Example | AATCC Spray[1] | Oil Kit[2] | Dry Soil[3] | Abrasion Test[4] 10X | 20X | 30X |
|---|---|---|---|---|---|---|
| 22 | 50− | 4 | 70 | 2 | 2 | 2 |
| 23 | 50− | 4.5 | 60 | 0 | 0 | 0 |
| 25 | 50 | 4 | 70 | 3 | 3 | 2 |
| 26 | 50 | 3 | 65 | 3 | 3 | 3 |
| 32 | 50− | 2 | 80 | 2 | 2 | 2 |
| 33 | 50− | 0 | 65 | 0 | 0 | 0 |
| 34 | 80− | 0 | 80 | 0 | 0 | 0 |
| Untreated | 0 | 0 | 0 | 0 | 0 | 0 |

[1]Spray Rating Method AATCC 22-1985
[2]Oil Kit Rating Method AATCC 118-1983
[3]Dry Soiling Test - CIBA-GEIGY Internal Test
[4]AATCC Abrasion Test AATCC 8-1985

In the above examples, the dry soil rating of greater than 50 demonstrates a substantial resistance to soil staining. The retention of an oil kit (>0) upon abrasion shows the durability of the finishes. The finishes render the untreated fabric water repellent ($A^2$ spray >0).

EXAMPLE 38

The 1,4-butanediol diglycidyl ether (2.01 g, 0.01 mols) and boron trifluoride etherate (0.20 g) are added to a 70° solution of $(C_8F_{17}CH_2CH_2SCH_2)_3CCH_2OH$ (30.00 g, 0.02 mols) in ethylene glycol dimethyl ether (48 g) under a nitrogen atmosphere. The reaction mixture is heated at 70° C. for 8 hours. The final product is obtained in 50% yield and contains a mixture of

VII $$(C_8F_{17}CH_2CH_2SCH_2)_3CCH_2O-CH_2\overset{OH}{\underset{|}{C}}HCH_2OC_4H_8OCH_2\overset{OH}{\underset{|}{C}}HCH_2-OCH_2C(CH_2SCH_2CH_2C_8F_{17})_3$$

-continued

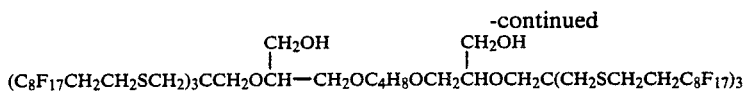

and

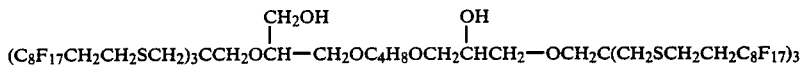

as determined by NMR.

EXAMPLE 39

The $(C_8F_{17}CH_2CH_2SCH_2)_3CCH_2OH$ (30.00 g, 0.02 mols) and ethylene glycol dimethyl ether (50.58 g) are heated at 70° under a nitrogen atmosphere to dissolve the fluorochemical. To this solution are added ARALDITE® GY-6010 (CIBA-GEIGY Corp., liquid diglycidyl ether of Bisphenol A, 3.72 g, 0.01 mols) and boron trifluoride etherate (0.20 g). The reaction mixture is heated at 70° for 8 hours. The final product is obtained in 50% yield and contains a mixture of

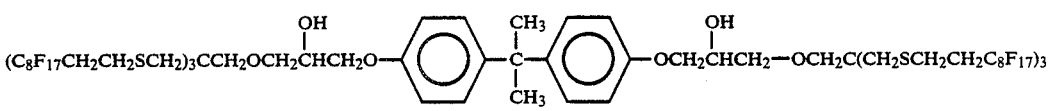

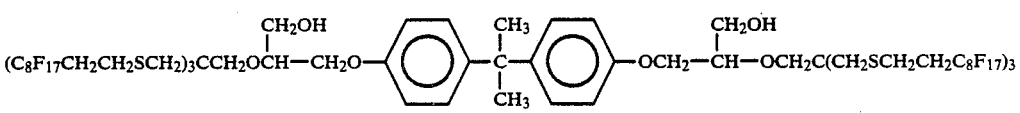

and

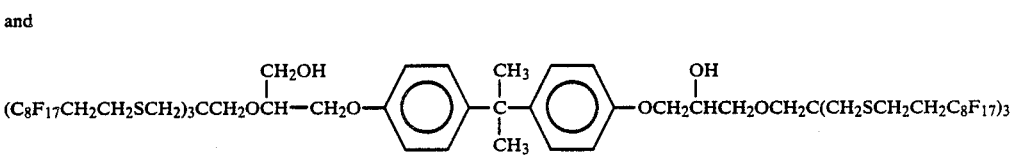

as determined by NMR.

What is claimed is:

1. A compound of formula I,

where

T is —OH, and wherein $R_f$ is independently a straight or branched chain perfluoroalkyl of 1 to 12 carbon atoms, perfluoroalkyl of 2 to 6 carbon atoms substituted by perfluoroalkoxy of 2 to 6 carbon atoms, or an oligo(hexafluoropropene oxide) terminal group, and n=1 or 0, and when n=1, E is independently a branched or straight chain alkylene of 1 to 10 carbon atoms or said alkylene interrupted by one to three groups selected from the group consisting of —NR—, —O—, —S—, SO$_2$—, —COO—, —OOC—, —CONR—, —NRCO—, —SO$_2$NR—, and —NRSO$_2$—, or terminated at the $R_f$ end with —CONR— or —SO$_2$NR—, where $R_f$ is attached to the carbon or sulfur atom, and X is —S—, or —SO$_2$—, and when n=0, X is a direct bond, —CONR— or —SO$_2$NR—, where $R_f$ is attached to the carbon or sulfur atom, and where R is independently hydrogen, alkyl of 1 to 6 carbon atoms or hydroxyalkyl of 2 to 6 carbon atoms.

2. A compound according to claim 1, wherein $R_f$ is independently a straight or branched chain perfluoroalkyl of 2 to 12 carbon atoms or perfluoroalkyl of 2 to 6 carbon atoms substituted by perfluoroalkoxy of 2 to 6 carbon atoms, or an oligo(hexafluoropropene oxide) chain, n=1 or 0, and when n=1, E is independently a branched or straight chain alkylene of 1 to 10 carbon atoms or said alkylene interrupted by one to three groups selected from the group consisting of —NR—, —O—, —S—, SO$_2$, —COO—, —OOC—, —CONR—, —NRCO—, —SO$_2$NR—, and —NRSO$_2$—, or terminated at the $R_f$ end with —CONR— or —SO$_2$NR—, where $R_f$ is attached to the carbon or sulfur atom, and X is —S— or —SO$_2$—, and when n=0, X is a direct bond, —CONR— or —SO$_2$NR—, where $R_f$ is attached to the carbon or sulfur atom, and where R is independently hydrogen, alkyl of 1 to 6 carbon atoms or hydroxyalkyl of 2 to 6 carbon atoms.

3. A compound according to claim 1 where $R_f$ is perfluoroalkyl of 6 to 12 carbon atoms or perfluoroalkyl of 2 to 6 carbon atoms substituted by perfluoroalkoxy of 2 to 6 carbon atoms, E is alkylene of 2 to 6 carbon atoms, —CONHCH$_2$CH$_2$—, —CH$_2$CH$_2$N(CH$_3$)CH$_2$CH$_2$—, —CH$_2$CH$_2$SO$_2$NHCH$_2$CH$_2$— or —SO$_2$NHCH$_2$CH$_2$—, and X is —S—, or —SO$_2$—.

4. A compound according to claim 1 wherein $R_f$ is perfluoroalkyl of 6 to 12 carbon atoms, E is ethylene, X is —S—.

5. A compound according to claim 1 which is $(C_6F_{13}CH_2CH_2SCH_2)_3CCH_2OH$.

6. A compound according to claim 1 which is $(C_8F_{17}CH_2CH_2SCH_2)_3CCH_2OH$.

7. A compound according to claim 1 which is $(C_7F_{15}CONHCH_2CH_2SCH_2)_3CCH_2OH$.

8. A compound according to claim 1 which is $[(CF_3)_2CFO(CF_2)_nCH_2CH_2SCH_2]_3CCH_2OH$ where n is 3 or 4.

9. A compound according to claim 1 which is $[(CF_3)_2CFOCF_2CH_2CH_2SCH_2]_3CCH_2OH$.

10. A compound according to claim 1 which is $(C_8F_{17}CH_2CH_2SO_2CH_2)_3CCH_2OH$.

11. A compound according to claim 1 which is $(R_fCH_2CH_2SCH_2)_3CCH_2OH$ where $R_f$ is a mixture of $C_4F_9$, $C_6F_{13}$, $C_8F_{17}$, and $C_{10}F_{21}$.

12. A compound according to claim 1 which is $(R_fSO_2N(C_2H_5)CH_2)_3CCH_2OH$.

* * * * *